United States Patent [19]

Cielo et al.

[11] Patent Number: 4,996,426
[45] Date of Patent: Feb. 26, 1991

[54] DEVICE FOR SUBSURFACE FLAW DETECTION IN REFLECTIVE MATERIALS BY THERMAL TRANSFER IMAGING

[75] Inventors: Paolo G. Cielo, Montréal; Xavier Maldague, Ste-Foy; Jean C. Krapez, Longueuil, all of Canada

[73] Assignee: National Research Council of Canada, Ottawa, Canada

[21] Appl. No.: 407,160

[22] Filed: Sep. 11, 1989

[51] Int. Cl.$^5$ .............................................. G01N 25/72
[52] U.S. Cl. ................................... 250/330; 250/342; 250/359.1; 374/5
[58] Field of Search ................... 250/342, 359.1, 358.1, 250/338.1, 330; 374/5

[56] References Cited

U.S. PATENT DOCUMENTS

| | | | |
|---|---|---|---|
| 3,020,745 | 2/1962 | Sielicki | 374/5 |
| 3,378,685 | 4/1968 | Green et al. | 250/341 |
| 3,427,861 | 7/1968 | Maley | 250/338.1 |
| 3,462,602 | 8/1969 | Apple | 250/338.1 |
| 3,504,524 | 4/1970 | Maley | 374/5 |
| 4,215,562 | 8/1980 | Gavrilin et al. | 374/5 |
| 4,480,168 | 9/1984 | Cielo et al. | 219/121.6 |

OTHER PUBLICATIONS

Cielo et al., "Thermographic Nondestructive Evaluation of Industrial materials and Structures", Materials Evaluation, Apr. 1987, vol. 45, 61, pp. 452 to 460.
Green, "Thermal and Infrared Nondestructive Testing of Composites and Ceramics", Materials Evaluation, 29 (11), Nov. 1971, pp. 241–248.
Maldague et al., "Subsurface Flaw Detection in Reflective Materials by Thermal-Transfer Imaging", Proceedings of the SPIE—The International Society for Optical Engineering, Mar. 1989, vol. 1094, pp. 163 to 173.

Primary Examiner—Carolyn E. Fields
Attorney, Agent, or Firm—Harold A. Kelly; Yoshiharu Toyooka

[57] ABSTRACT

Apparatus for nondestructive detection of subsurface defects in a continuously moving workpiece of sheet material by using an infrared thermal imager. The temperature of a portion of the surface of sheet material is altered and the presence of subsurface flaws is indicated by development of discontinuities in the surface temperature distribution above the defects. In order to avoid problems due to changes in the infrared emissivity of the surface of sheet material, such as caused by grease patches or oxidized areas as well as errors caused by reflections of other sources of infrared radiation from the surface, the thermal image of the portion is first transferred by contact to a surface of a thermal transfer device whose surface has a high infrared emissivity and a low infrared reflectivity. Then the thermal image of the portion is obtained from the surface of the thermal transfer device.

20 Claims, 1 Drawing Sheet ical sheets without any previous preparation or post-cleaning steps being necessary. This is accomplished by altering the temperature of a portion of the sheet to be tested and then transferring the thermal image produced by this portion of the sheet onto a surface of material with high infrared emissivity and low infrared reflectivity which material is brought into contact with the sheet. Once the thermal image from the sheet is transferred onto the surface of the high infrared emissivity material, an image of the temperature distribution can easily be acquired by an infrared camera without errors being caused by emissivity variations across the metal surface or by spurious reflections from bodies in the background.

DEVICE FOR SUBSURFACE FLAW DETECTION IN REFLECTIVE MATERIALS BY THERMAL TRANSFER IMAGING

FIELD OF THE INVENTION

The present invention is directed to an apparatus to detect hidden subsurface defects such as an inclusion in a continuously moving sheet or a delamination or lack of bonding in a laminated sheet structure during or after manufacture of the sheet. One possible approach for the nondestructive inspection of a workpiece, such as a sheet or laminated sheet structure, for defects makes use of an infrared thermal imager. In an infrared nondestructive testing system, the temperature of the workpiece is altered and the presence of subsurface flaws is indicated by development of discontinuities in the surface temperature distribution above the defects.

BACKGROUND OF THE INVENTION

Means to inject thermal energy into a workpiece for the nondestructive testing of that workpiece include lamp radiators as described in U.S. Pat. No. 3,427,861; hot-air guns as described in U.S. Pat. No. 3,378,685 or induction heaters as described in U.S. Pat. No. 4,215,562. Alternatively, the previously heated or naturally hot material of the workpiece may be surface cooled by a cool-air or water jet as described in U.S. Pat. No. 3,462,602. In this case, a thermal discontinuity over the defect will develop when the cold thermal front reaches subsurface flaws.

Methods to map the temperature distribution over the workpiece include single or double infrared sensors as described in U.S. Pat. Nos. 3,378,685 and 3,462,602, scanned detector images as described in U.S. Pat. No. 3,427,861 or thermosensitive coatings as described in U.S. Pat. No. 4,215,562. In modern thermal imaging systems, an infrared (IR) camera is used to continuously display the surface temperature of a thermally excited workpiece for inspecting relatively large areas at a fast pace.

Infrared inspection systems are difficult to apply to the nondestructive testing of materials having highly reflective surfaces, such as metallic sheets or aluminum-to-aluminum adhesively bonded panels of the kind used in the transportation and aeronautical industries. Metallic surfaces have a low light absorptivity and a low infrared emissivity coefficient, typically 5% of the emissivity of a black body. The infrared power radiated by a heated metallic workpiece is exceedingly low, giving a faint thermal image. In addition, the presence of grease patches or slightly oxidized areas on the metal surface may easily change the local surface emissivity from 5 to 10 or even 20% of that of the black body emissivity creating apparent "hot spots" on the infrared image which may be interpreted as defective areas. Moreover, the high reflectivity of the metallic surfaces introduces a reflection noise problem, whereby infrared radiation emitted by warm bodies in the background is reflected by a metal surface of the sheet which acts as a smooth mirror in the long-wavelength infrared region. The reflected image super-imposes itself onto the infrared emission image introducing further spurious "hot spots" and thus further complicating the interpretation of the thermal image provided by the infrared camera.

One possible approach to overcome these problems requires painting a black coating on the metallic surface prior to inspection. The black painted surface has a uniformly high infrared emissivity independently of the presence of grease patches, while its infrared reflectivity and thus the interference problems from nearby warm bodies is exceedingly low. However, the introduction of a painting step and of a subsequent cleaning step is quite inconvenient in an inspection procedure whose main interest is its high inspection speed.

Another possible approach to reduce low-emissivity problems is the use of a reflective cavity, such as the hemispheric cavity described in U.S. Pat. No. 4,480,168. Although being appropriate for the average temperature sensing of a given area, this approach is inadequate for thermal imaging because multiple reflections within the cavity tend to average out the infrared radiation emitted by the whole surface enclosed by the cavity.

SUMMARY OF THE INVENTION

The present invention provides means for overcoming the above-mentioned difficulties More particularly, the present invention discloses a nondestructive infrared testing apparatus particularly well adapted to the high speed inspection of large sheets such as highly reflective metal In order that the inspection process can be carried out without interruption at a very high surface coverage rate, means are provided to assure a good thermal contact of the infrared high-emissivity material with the continuously moving surface of the sheet. Preferred embodiments are ones using either a single roller made of an infrared high-emissivity resilient black material or a moving closed-loop black membrane whose surface is placed in contact with the surface of the sheet by means of rollers which press a portion of the closed-loop membrane against the surface of the sheet.

BRIEF DESCRIPTION OF THE DRAWINGS

The features and advantages of the present invention will become more readily apparent in the following detailed description of the invention taken in conjunction with the accompanying drawings wherein.

DESCRIPTION OF THE PREFERRED EMBODIMENTS

Figure 1:
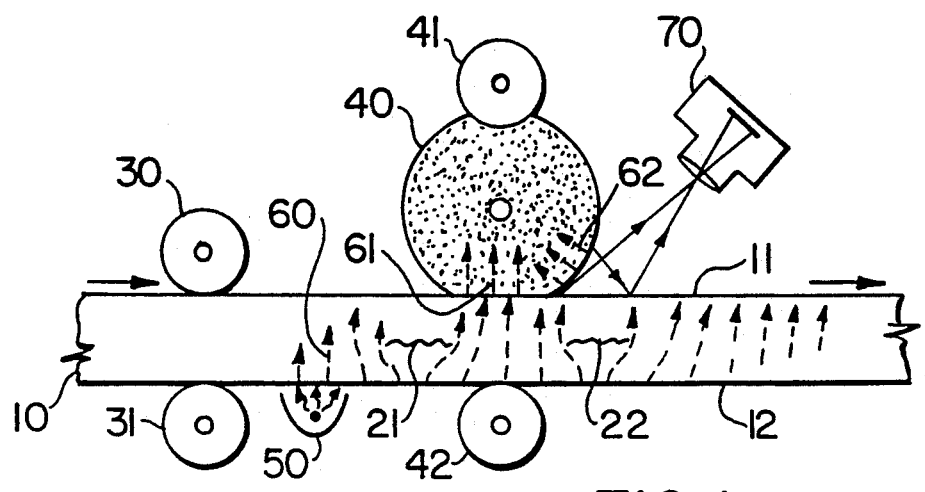
FIG. 1 illustrates a general arrangement of an infrared nondestructive testing system using a thermal-image transfer method in accordance with the present invention.

A schematic diagram of a thermal-transfer nondestructive testing system according to the present invention is shown in FIG. 1. The continuous sheet 10 which is to be inspected, typically an assembly of layers adhesively bonded between top and the bottom metallic surfaces 11 and 12, may contain hidden flaws 21 or 22 in the form of delaminations between two adjacent layers. The sheet 10 is driven by rollers 30 and 31 through the continuous nondestructive inspection station which includes a series of rollers 40, 41 and 42 as well as a heating lamp 50 extending across the width of the sheet.

The lower surface 12 is heated when passing over the heat source 50 and thermal energy then flows from the lower surface 12 to the upper surface 11 of the sheet 10 along thermal flow lines 60. If the thermal flow encounters low thermal conductivity defects 21 or 22 along its path, the thermal flow lines will deviate to circumvent said defects, leaving relatively cooler areas on regions of the upper surface 11 which are above the defects. In a conventional infrared nondestructive detection system, an infrared camera is used to display the temperature distribution across the upper surface 11 of the sheet, and the observation of "cold spots" on the surface 11 is related to the presence of defects immediately below the cooler region. Alternatively, the infrared camera may be pointed towards the bottom surface 12 of the sheet 10 which has been heated by the heat source 50. In this case, defects will manifest themselves by relatively warmer areas "hot spots" appearing under the low thermal conductivity defects since the defects hinder the flow of thermal energy towards the interior of the material.

The difficulty in detecting hidden defects in metallic structures using conventional systems will be apparent if it is considered that the temperature differentials which develop between defect related "hot" or "cold" spots as compared to defect-free areas are usually in the range of a fraction of 1° C. Although modern IR cameras have sensitivites of the order of 0.1° C. when pointed towards high-emissivity surfaces such as materials painted black, their sensitivity become worse by an order of magnitude when a low-emissivity bare metal surface is inspected. Moreover, apparent temperature fluctuations of several degrees C. may be introduced when the infrared radiation from a nearby warm body, a body such as a power machine, is reflected by the metallic surface towards the camera.

The system according to the present invention overcomes such problems by inserting along an inspection line for the sheet 10, a soft resilient black roller 40 which, together with the auxiliary metallic rollers 41 and 42, is freely rotatable so as to be in continuous good thermal contact with the upper surface 11 of the sheet 10. Thermal energy flows from the surface 11 of the metal sheet to the resilient cylinder 40 following thermal energy flow line 61 so that, after contact with the sheet, the temperature distribution over the surface of the resilient cylinder 40 exactly reproduces the temperature distribution over the surface 11 of the metallic sheet. The temperature distribution can be conveniently observed by pointing the infrared camera 70 towards the surface of the roller 40 either directly or through a reflection from the highly reflective metallic surface 11 as shown in FIG. 1. Because of the high infrared emissivity of the resilient roller 40, preferably made of a black rubber material, the displayed thermal image has a high intensity and is unaffected by background reflections due to the low reflectivity of the black roller surface.

The resilient roller 40 may be made of a carbon-powder-filled foam polymer, with a large number of gas bubbles insuring a high degree of resilience and a relatively small thermal conductivity. In the region of the roller 40 which is in contact with the sheet surface 11, the gas bubbles inside the foam material are compressed by action of the applied pressure. This results in a good thermal flow within the cylindrical roller along flow lines 61 during the relatively short contact time period. After the contact time period, the gas bubbles in the foam are re-established to their original size, thus assuring a relatively low thermal conductivity and a weak thermal flow along flow lines 62. As a consequence, the transferred thermal image will remain for a relatively long time and with good contrast on the surface of roller 40 where it can be easily observed by the IR camera 70.

The auxiliary roller 41 presses roller 40 against the sheet and is preferably made of a highly thermal conductive metal such as copper in order to effectively erase the thermal image upon the surface of the resilient roller 40 during its contact with the highly conductive roller 41. The roller 41 could be replaced with an air-jet curtain, but the use of a contacting roller is preferred because it insures a better temperature uniformity along the resilient roller 40.

Many variations of the configuration shown in FIG. 1 are possible. For example, the heating lamp 50 could be above the sheet and the resilient roller 40 below the sheet. This configuration could help to keep the inspected sheet surface and thus the surface of the roller 40 free from dust or other particles. The heat lamp 50 could be replaced by a hot-air or hot-water jet, or else a cool-air or cold-water jet to produce a negative surface temperature image of the inspected sheet. If the sheet is relatively thick and the subsurface defects to be detected are close to the upper surface 11 of the sheet, a better thermal contrast will be obtained by placing the thermal source 50 above the top surface 11 of the sheet, just before contact with the resilient roller 40. Masks will then be used between the thermal source 50 and the resilient roller 41 to prevent the roller temperature being raised by the heat source prior to contacting the top surface 11. Alternatively, for very shallow defects, the thermal source may be eliminated by keeping the temperature of the auxiliary roller 41 at a temperature different from the temperature of the sheet 10. The temperature distribution within a shallow depth will, in this case, be introduced on the sheet during the short period of contact with the roller 40. Furthermore, the two-dimensional IR camera could be replaced by a line-scanned infrared detector or by an array of single-spot sensors.

The system shown in FIG. 1 is particularly useful for the inspection of relatively thin, sheet-like materials when access to both sides of the sheet is readily available or else for the detection of shallow defects in a relatively thick workpiece when both the thermal source and the thermal transfer roller are on the same side of the workpiece. The defects must have a depth range which is of the order of the propagation distance of the thermal front during the time period elapsed between the application of the thermal source 50 and the surface temperature pickup by the roller 40. In the latter case, the distance between said thermal source and said roller must be appropriately chosen in relation with the expected depth range of the defects.

Figure 2:
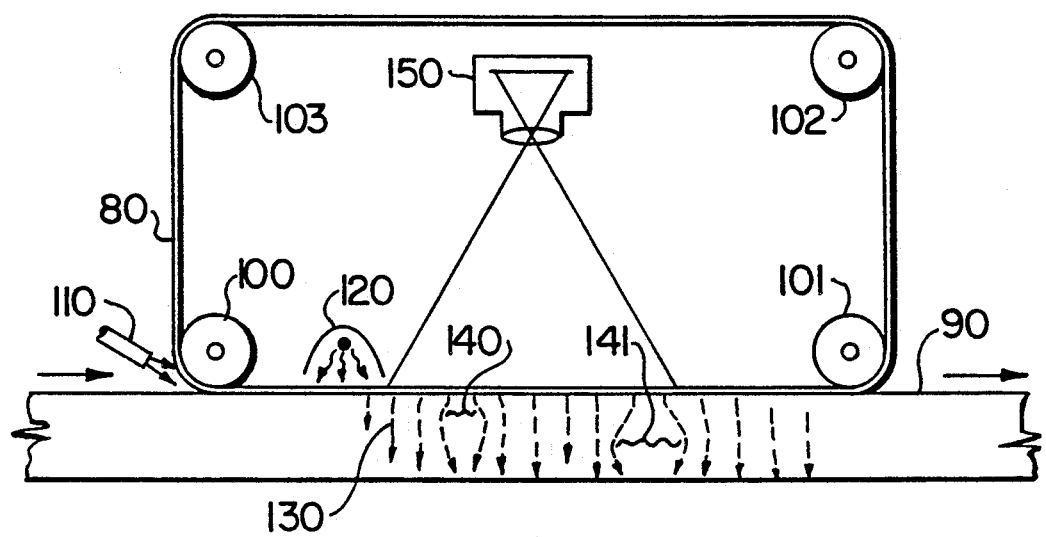
FIG. 2 illustrates a modification of the arrangement using a closed-loop black membrane moving over rollers which press the membrane against the workpiece to acquire the thermal image from the continuously moving workpiece.

When a predetermined defect depth range cannot be fixed, the defect depth being completely unknown, a modified version of the nondestructive testing system may be used as illustrated in FIG. 2. In this case, a closed-loop membrane 80, preferably a thin black plastic sheet, is kept in close contact with the surface 90 of the sheet to be inspected by a system of rollers 100, 101, 102 and 103. A modest-flow water jet 110 may be used to produce, by capillarity, a thin liquid film between the membrane 80 and the surface 90 so as to insure a good thermal contact between these surfaces. After heating by thermal source 120, thermal energy flows within the workpiece along flow lines 130 which are eventually distorted by the presence of subsurface defects 140 and 141 leaving hot or cold spots on the membrane surface which are observed by an IR camera 150. The temperature distribution recorded by the camera is displayed in a form substantially similar to the thermal image display in FIG. 1. Cross-correlation between subsequent time frames may be used to reduce random noise from the displayed images. Moreover, in the case of FIG. 2, the time delay of maximum defect visibility after thermal heating may be used to evaluate the depth Z of the defect following the relation:

$$Z \sim (\alpha t)^{\frac{1}{2}}$$

where $\alpha$ is the thermal diffusivity of the inspected material and t is the elapsed time, following the theory developed in more detail in the document "Thermographic Nondestructive Evaluation of Industrial Materials and Structures" by P. Cielo, X. Maldague, A. A. Déom and R. Lewak in Materials Evaluation, April 1987, Vol. 45, pages 52 to 460.

The presence of air bubbles or other thermal discontinuities at the interface between the membrane and the workpiece may be differentiated from internal defects by observing that the visibility of interface defects does not develop during the advance of the workpiece.

Minor modifications to the preferred embodiment shown in FIG. 2 may be introduced without substantial departure from the basic principles. For example, the heat lamp 120 may be substituted by a hot or cold air gun to introduce the required thermal perturbation or else the change in temperature could be directly introduced by the water jet 110 or by roller 100 by keeping such components at a temperature substantially higher or lower than the initial equilibrium temperature of the sheet 90.

These and other modifications of the preferred embodiments can be carried out without departing from the spirit and scope of the present invention which is determined in accordance with the appended claims.

We claim:

1. A thermal-imaging apparatus for the non-destructive detection in a continuously moving workpiece of sheet material comprising:
   means to change the temperature of a portion of a surface of the workpiece to a temperature different from its initial equilibrium temperature,
   a continuously recyclable thermal transfer device having a movable surface, which movable surface has a high infrared emissivity and a low infrared reflectivity,
   a device to press said thermal transfer device against said portion to provide good thermal contact between said movable surface and said portion whereby a thermal image of said portion is transferred to said movable surface, and
   means to produce a thermal image of said portion from said movable surface of said thermal transfer device.

2. A thermal-imaging apparatus as defined in claim 1, wherein said thermal transfer device is a resilient, rotatable roller having a surface with a high infrared emissivity and low infrared reflectivity, the roller comprising means for contacting the surface of the continuously moving workpiece.

3. A thermal-imaging apparatus as defined in claim 2, wherein said roller is formed of black rubber material.

4. A thermal-imaging apparatus as defined in claim 2, wherein said roller is formed of a carbon powder filled foam polymer assuring a higher thermal flow during contact with said workpiece and a lower thermal flow after contact.

5. A thermal-imaging apparatus as defined in claim 2, wherein the means to produce a thermal image is an infrared camera arranged to produce a thermal image of a section of the surface of the rotatable roller.

6. A thermal-imaging apparatus as defined in claim 2, wherein the rotatable roller is pressed into contact with the surface of the workpiece by a further roller, the further roller being formed of a material with a high thermal conductivity to erase surface temperature discontinuities on the surface of said rotatable roller.

7. A thermal-imaging apparatus as defined in claim 2, wherein the workpiece has a highly reflective surface which reflects a thermal image of a section of the surface of the rotatable roller and wherein an infrared camera comprises means for receiving the reflected thermal image.

8. A thermal-imaging apparatus as defined in claim 2, wherein the means to change the temperature of a surface portion of the workpiece is a heat lamp.

9. A thermal-imaging apparatus as defined in claim 2, wherein the means to change the temperature of a surface portion of the workpiece is a fluid jet.

10. A thermal-imaging apparatus as defined in claim 1, wherein said thermal transfer device is a closed-loop membrane located on rollers, which rollers comprise means for pressing the membrane against a surface of the moving workpiece.

11. A thermal-imaging apparatus as defined in claim 10, wherein said closed-loop membrane is a black plastic sheet.

12. A thermal-imaging apparatus as defined in claim 10, wherein the means to change the temperature of a surface portion of the workpiece is a heat lamp.

13. A thermal-imaging apparatus as defined in claim 10, wherein the means to change the temperature of a surface portion of the workpiece is a fluid jet located adjacent to a first roller which initially presses said membrane against said workpiece.

14. A thermal-imaging apparatus as defined in claim 10, wherein a liquid jet is located adjacent a first roller which initially presses said membrane against said workpiece, the jet comprising means for inserting a film of liquid between the surface of the membrane and the surface of the workpiece to ensure a good thermal contact between the surface of the workpiece and the membrane.

15. A thermal-imaging apparatus as defined in claim 10, wherein the means to change the temperature of a surface portion of the workpiece is a heat lamp located adjacent a first roller which initially presses said membrane against said workpiece, the lamp being located between the first roller and a second roller, the second roller allowing the membrane to be removed from contact with the surface of the workpiece.

16. A thermal-imaging apparatus as defined in claim 15, wherein the means to produce a thermal image is an infrared camera located between the heat lamp and the second roller, the infrared camera being arranged to produce an infrared image of a section of the membrane in contact with the workpiece.

17. A method for non-destructively detection of defects in a continuously moving workpiece of sheet material comprising:

introducing a change of temperature on a portion of a surface of said workpiece, establishing a transient contact between said portion whose temperature was changed and a surface of a thermal transfer medium which has a high infrared emissivity and low infrared reflectivity, and producing a thermal image of the temperature distribution on the surface of the thermal transfer medium after the transient contact with the surface of workpiece.

18. A method for the nondestructive detection of defects in a continuously moving workpiece of sheet material as defined in claim 17, wherein the thermal transfer medium is a resilient, rotatable roller which contacts the surface of the continuously moving workpiece and the rotatable roller is pressed into contact with the surface of the workpiece by a further roller, the further roller being formed of a material with a high thermal conductivity to erase surface temperature discontinuities on the surface of said rotatable roller.

19. A method for the non-destructive detection of defects in a continuously moving workpiece of sheet material having at least one metallic surface by establishing a thermal contact between the metallic surface and a closed-loop movable membrane having a high infrared emissivity and low infrared reflectivity by pressing a portion of the closed-loop membrane against the metallic surface, which portion moves with said surface for a predetermined distance;

introducing a thermal change on a surface of the membrane at a predetermined location and providing an image of the temperature evolution along the surface of the membrane within said predetermined distance.

20. A method for the non-destructive detection of defects in a continuously moving workpiece of sheet material as defined in claim 19, wherein the thermal contact between the membrane and metallic surface is increased by injecting a liquid layer between the membrane and metallic surface at the interface where the membrane initially contacts the metallic surface.

* * * * *